US00PP19689P2

(12) United States Plant Patent
Murakami

(10) Patent No.: US PP19,689 P2
(45) Date of Patent: Feb. 10, 2009

(54) ***NIEREMBERGIA* PLANT NAMED 'SUNNICOPADIBU'**

(50) Latin Name: *Nierembergia hybrida*
Varietal Denomination: Sunnicopadibu

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/079,270

(22) Filed: Mar. 25, 2008

(51) Int. Cl.
*A01H 5/00* (2006.01)

(52) U.S. Cl. ..... Plt./459
(58) Field of Classification Search ..... Plt./459
See application file for complete search history.

*Primary Examiner*—Annette H Para
(74) *Attorney, Agent, or Firm*—C. A. Whealy

(57) ABSTRACT

A new and distinct cultivar of *Nierembergia* plant named 'Sunnicopadibu', characterized by its compact, upright and mounding plant habit; freely branching habit; freely and continuous flowering habit; large dark purple violet-colored flowers; long flowering period; and good garden performance.

1 Drawing Sheet

Botanical designation: *Nierembergia hybrida.*
Cultivar denomination: 'Sunnicopadibu'.

BACKGROUND OF THE INVENTION

The present invention relates to a new and distinct cultivar of *Nierembergia,* botanically known as *Nierembergia hybrida* and hereinafter referred to by the name 'Sunnicopadibu'.

The new *Nierembergia* is a product of a planned breeding program conducted by the Inventor in Higashiomi, Shiga, Japan. The objective of the breeding program was to create new compact *Nierembergia* cultivars with attractive flower coloration.

The new *Nierembergia* originated from a cross-pollination made by the Inventor during the summer of 2003, in Higashiomi, Shiga, Japan, of a proprietary selection of *Nierembergia hybrida* identified as code number N121, not patented, as the female, or seed, parent with a proprietary selection of *Nierembergia hybrida* identified as code number NB18, not patented, as the male, or pollen, parent. The new *Nierembergia* was discovered and selected by the Inventor as a single flowering plant within the progeny of the stated cross-pollination in a controlled environment in Higashiomi, Shiga, Japan.

Asexual reproduction of the new *Nierembergia* by vegetative cuttings in a controlled environment in Higashiomi, Shiga, Japan since October, 2005, has shown that the unique features of this new *Nierembergia* are stable and reproduced true to type in successive generations.

SUMMARY OF THE INVENTION

The cultivar Sunnicopadibu has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunnicopadibu'. These characteristics in combination distinguish 'Sunnicopadibu' as a new and distinct cultivar of *Nierembergia:*

1. Compact, upright and mounding plant habit.
2. Freely branching habit.
3. Freely and continuous flowering habit.
4. Large dark purple violet-colored flowers.
5. Long flowering period.
6. Good garden performance.

Plants of the new *Nierembergia* differ from plants of the female parent selection in the following characteristics:

1. Plants of the new *Nierembergia* have thinner stems than plants of the female parent selection.
2. Plants of the new *Nierembergia* have broader leaves than plants of the female parent selection.
3. Plants of the new *Nierembergia* flower earlier than plants of the female parent selection.
4. Plants of the new *Nierembergia* and the female parent selection differ in flower color as plants of the female parent selection have light blue-colored flowers.

Plants of the new *Nierembergia* differ from plants of the male parent selection in the following characteristics:

1. Plants of the new *Nierembergia* are more freely branching than plants of the male parent selection.
2. Plants of the new *Nierembergia* have thinner stems than plants of the male parent selection.
3. Plants of the new *Nierembergia* flower earlier than plants of the male parent selection.

Plants of the new *Nierembergia* can be compared to plants of the cultivar Sunniparisobu, disclosed in U.S. Plant Pat. No. 16,394. In side-by-side comparisons conducted in Higashiomi, Shiga, Japan, plants of the new *Nierembergia* and the cultivar Sunniparisobu differed in the following characteristics:

1. Plants of the new *Nierembergia* were shorter than plants of the cultivar Sunniparisobu.
2. Plants of the new *Nierembergia* had shorter internodes than plants of the cultivar Sunniparisobu.
3. Plants of the new *Nierembergia* had smaller leaves than plants of the cultivar Sunniparisobu.

4. Plants of the new *Nierembergia* flowered earlier than plants of the cultivar Sunniparisobu.
5. Plants of the new *Nierembergia* had smaller flowers than plants of the cultivar Sunniparisobu.
6. Plants of the new *Nierembergia* had darker colored flowers than plants of the cultivar Sunniparisobu.

BRIEF DESCRIPTION OF THE PHOTOGRAPHS

The accompanying colored photographs illustrate the overall appearance of the new *Nierembergia,* showing the colors as true as it is reasonably possible to obtain in colored reproductions of this type. Colors in the photographs may differ slightly from the color values cited in the detailed botanical description which accurately describe the colors of the new *Nierembergia.*

The photograph at the top of the sheet comprises a side perspective view of a typical flowering plant of 'Sunnicopadibu' grown in a container.

The photograph at the bottom of the sheet is a close-up view of typical flowers and leaves of 'Sunnicopadibu'.

DETAILED BOTANICAL DESCRIPTION

The aforementioned photographs and following observations, measurements and values describe plants grown in Higashiomi, Shiga, Japan, under commercial practice during the summer in an outdoor nursery with day temperatures averaging 23° C. and night temperatures averaging 13° C. After planting, plants had been growing for about four months when the photographs and description were taken. In the following description, color references are made to The Royal Horticultural Society Colour Chart, 2001 Edition, except where general terms of ordinary dictionary significance are used.

Botanical classification: *Nierembergia hybrida* cultivar Sunnicopadibu.

Parentage:

*Female, or seed, parent.*—Proprietary selection of *Nierembergia hybrida* identified as code number N121, not patented.

*Male, or pollen, parent.*—Proprietary selection of *Nierembergia* hybrida identified as code number NB18, not patented.

Propagation:

*Type.*—By vegetative cuttings.

*Time to initiate roots.*—About two weeks at 20° C. to 25° C.

*Time to produce a rooted young plant roots.*—About 35 days at 20° C. to 25° C.

*Root description.*—Fine, fibrous, fleshy; white in color.

*Rooting habit.*—Freely branching.

Plant description:

*Plant form/habit.*—Compact, upright and mounded plant habit; outwardly spreading; moderately vigorous growth habit. Freely branching habit; pinching enhances branching potential.

*Plant height.*—About 18 cm.

*Plant width* (*spread*).—About 24.4 cm.

*Lateral branches.*—Length: About 16.6 cm. Diameter: About 1.4 mm. Internode length: About 6 mm. Strength: Strong. Texture: Sparsely pubescent. Color: Close to 137B.

Foliage description:

*Arrangement.*—Alternate, simple; sessile.

*Length.*—About 2.7 cm.

*Width.*—About 2.6 mm.

*Shape.*—Lanceolate.

*Apex.*—Acute.

*Base.*—Attenuate.

*Margin.*—Entire.

*Texture, upper and lower surfaces.*—Pubescent.

*Venation pattern.*—Pinnate.

*Color.*—Developing leaves, upper and lower surfaces: Close to 144A. Fully expanded leaves, upper and lower surfaces: Close to 137C; venation, close to 137C.

Flower description:

*Flower type/habit.*—Single salverform flowers; flowers face mostly upright. Freely flowering habit with about 30 flowers developing per plant.

*Fragrance.*—None detected.

*Natural flowering season.*—Long and continuous flowering habit from spring to late autumn in Higashiomi, Shiga, Japan. Flowers not persistent.

*Postproduction longevity.*—Flowers last about five days on the plant.

*Flower buds.*—Height: About 2.5 cm. Diameter: About 5.4 mm. Shape: Clavate. Color: Close to 86D.

*Flower diameter.*—About 3 cm.

*Flower depth.*—About 1.4 cm.

*Petals.*—Quantity per flower: Typically five in a single whorl; petals fused. Length: About 1.4 cm to 1.8 cm. Lobe width: About 1.6 cm. Tube length: About 1.7 cm. Tube diameter: About 1.4 mm. Shape: Roughly spatulate. Apex: Obtuse. Margin: Entire; slightly undulate. Texture, upper and lower surfaces: Smooth, glabrous. Texture, tube: Smooth, glabrous. Color: Developing and fully expanded petals, upper surface: Close to N81A; towards the center, 5A. Developing and fully expanded petals, lower surface: Close to 84A. Throat: Close to 1C. Tube: Close to 1C.

*Sepals.*—Quantity per flower: Typically five in a single whorl, fused at base; star-shaped calyx. Length: About 7.1 mm. Width: About 2.1 mm. Shape: Lanceolate. Apex: Acute. Margin: Entire. Texture, upper and lower surfaces: Smooth, glabrous. Color, upper and lower surfaces: Close to 137B.

*Peduncles.*—Length: About 4 mm. Diameter: About 0.8 mm. Texture: Smooth, glabrous. Color: Close to 137B.

*Reproductive organs.*—Stamens: Quantity per flower: Typically five. Stamen length: About 7.1 mm. Anther shape: Globose. Anther size: About 1.4 mm by 1 mm. Anther color: Close to 10B. Pollen amount: Moderate. Pollen color: Close to 6A. Pistils: Quantity per flower: One. Pistil length: About 2.1 cm. Stigma shape: Globose. Stigma color: Close to 144C. Style color: Close to 145C. Ovary color: Close to 137A.

*Seed/fruit.*—Seed and fruit development have not been observed.

Disease/pest resistance: Plants of the new *Nierembergia* have not been noted to be resistant to pathogens and pests common to *Nierembergia.*

Garden performance: Plants of the new *Nierembergia* have been observed to have good garden performance and tolerate rain, wind and temperatures from about −8° C. to about 35° C.

It is claimed:

1. A new and distinct *Nierembergia* plant named 'Sunnicopadibu' as illustrated and described.

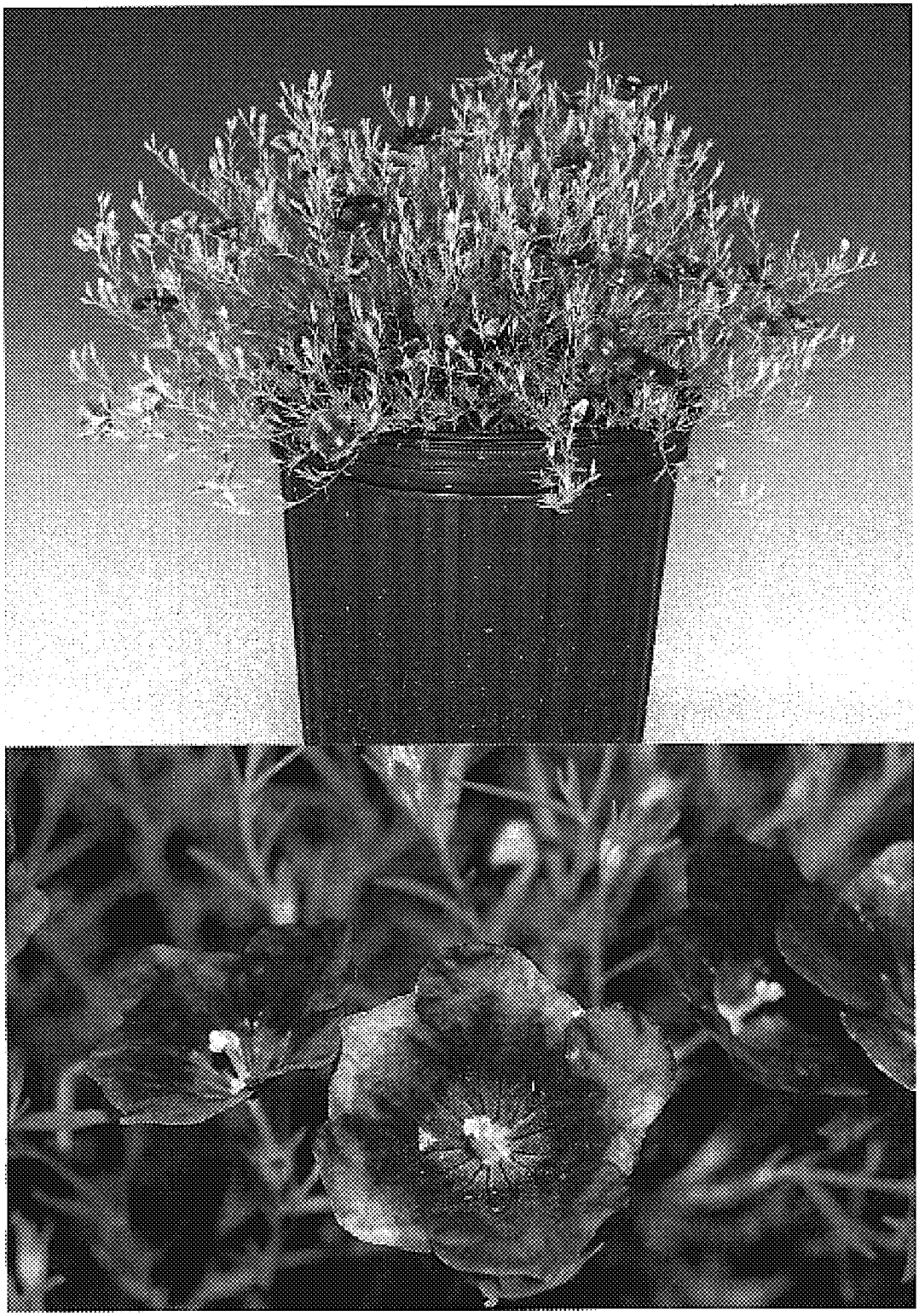

* * * * *